(12) United States Patent
Sparhawk, Jr.

(10) Patent No.: US 6,322,503 B1
(45) Date of Patent: Nov. 27, 2001

(54) METHOD OF DIAGNOSING, TRACKING, AND TREATING DEPRESSION

(76) Inventor: G. Roger Sparhawk, Jr., 10015 Crestridge Dr., Chardon, OH (US) 44024

(*) Notice: Subject to any disclaimer, the term of this patent is extended or adjusted under 35 U.S.C. 154(b) by 0 days.

(21) Appl. No.: 09/506,660

(22) Filed: Feb. 17, 2000

(51) Int. Cl.⁷ .................................................. G09B 19/00
(52) U.S. Cl. ............................ 600/300; 600/558; 600/559; 434/236
(58) Field of Search ......................... 600/300–301, 600/544–546, 558–559; 434/236; 128/898–897, 920, 925

(56) References Cited

U.S. PATENT DOCUMENTS

| | | | |
|---|---|---|---|
| 4,346,697 | * | 8/1982 | Cohen .................................. 600/300 |
| 5,473,537 | * | 12/1995 | Glazer et al. ........................ 600/300 |
| 5,882,203 | * | 3/1999 | Correa et al. ........................ 434/236 |
| 6,053,866 | * | 4/2000 | McLeod ............................... 600/300 |
| 6,165,126 | * | 12/2000 | Merzenich et al. ................... 600/300 |
| 6,206,829 | * | 3/2001 | Iliff ..................................... 600/300 |

* cited by examiner

Primary Examiner—Eric F. Winakur
Assistant Examiner—Michael C Astorino (57) ABSTRACT

The present invention relates to a method of diagnosing, tracking, and rating depressive symptoms in order to predict responses to specific treatments and guide further adjustments and interventions to treatments. The present invention permits rapid and meaningful depressive symptom severity ratings even when conventional or verbal symptom descriptions are difficult or impossible. The present invention further provides a means for detecting and quantifying intense emotional pain, including depression subtypes and major depressions with psychotic features. The present invention also provides a means of quantitative comparisons for the results of successive treatment trials. The present invention covers the whole range of depression symptom diagnosis and requires no literacy or minimal mental capacities from the patients. Furthermore, the present invention minimizes bias in order to avoid over or under diagnosis and treatments. In addition, the present invention provides a method by which immediate feedback and/or immediate outcome data may be gathered regarding the existence or non-existence of depressive symptoms in an individual.

25 Claims, 7 Drawing Sheets

| 60 | | | |
|---|---|---|---|
| Date Elicited | | | |
| Despair Cluster | | | |
| 1. Emot. Pain | 611 | | Emotional Pain |
| 2. NeverGetBetter | 612 | | Feelings You will Never Get Better from the Depression |
| 3. Overwhelm | 613 | | Feeling Overwhelmed |
| 4. Hopeless | 614 | | Feelings of Hopelessness |
| 5. Fear | 615 | | Fear |
| Melancholia Cluster | | | |
| 6. Worse A.M. | 621 | | Depression Regularly Worse in the Morning |
| 7. Retard/Agit | 622 | | Marked Psychomotor Retardation or Agitation |
| 8. Weight Loss | 623 | | Significant Weight Loss |
| 9. Exc./InapGuilt | 624 | | Excessive or Inappropriate Guilt |
| MCPF Cluster | | | |
| MCPF Delus: | 631 | | Mood-Congruent Delusions |
| 10. Inadequacy | 632 | | Delusions of Inadequacy |
| 11. Guilt | 633 | | Delusions of Guilt |
| 12. Dis/Death | 634 | | Delusions of Death or Disease |
| 13. Nihilism | 635 | | Nihilistic Delusions |
| 14. DsvPunish | 636 | | Delusions of Deserved Punishment |
| 15. Halluc | 637 | | Hallucinations |
| MIPF Cluster | | | |
| MIPF Delus: | 641 | | Mood-Incongruent Delusions |
| 16. Persecut | 642 | | Delusions of Persecution |
| 17. ThtIns/Brdcast | 643 | | Thought Insertion/Thought Broadcasting |
| 18. Control | 644 | | Delusions of Control |
| 19. Suspic | 645 | | Suspiciousness |
| 20. IdeasOfRef | 646 | | Ideas of Reference |
| 21. Halluc | 647 | | Hallucinations |
| 22. | | | |
| 23. | | | |
| 24. | | | |
| 25. PsychMeds | | | Psychotropic Medications |
| (mg/day) | | | (milligrams per day) |
| 26. Other Meds | | | Other Medications |

| Date Elicited | | | | | | | | |
|---|---|---|---|---|---|---|---|---|
| 1. Depress. | | | | | | | | |
| 2. Anxiety | | | | | | | | |
| 3. ApptDist. | | | | | | | | |
| 4a.. Slp. Dist. | | | | | | | | |
| 4b. Slp H/24 | | | | | | | | |
| 4c. Slp Char. | | | | | | | | |
| 4d. MCA/7 | | | | | | | | |
| EMA/7 | | | | | | | | |
| 5. Disint. | | | | | | | | |
| 6. Anhedonia | | | | | | | | |
| 7. Libido | | | | | | | | |
| 8. Energy | | | | | | | | |
| 9. Thk/Conc. | | | | | | | | |
| 10. W.S.-B.G. | | | | | | | | |
| 11. Death | | | | | | | | |
| 12. Suicide | | | | | | | | |
| 13. SHPI | | | | | | | | |
| 14. N vs T | | | | | | | | |
| | | | | | | | | |
| 15. PsyTrop. | | | | | | | | |
| (mg/day) | | | | | | | | |
| | | | | | | | | |
| 16. OtherMeds | | | | | | | | |
| | | | | | | | | |
| 17. Side Effs. | | | | | | | | |
| | | | | | | | | |
| 18. Context | | | | | | | | |
| | | | | | | | | |
| 19. ?'s/Loose Ends | | | | | | | | |
| (Use OPTIONAL Clusters below only if these syndromes are suspected or diagnosed) | | | | | | | | |
| (D.1. LwSlfEstm) | | | | | | | | |
| (D.2. Indecision) | | | | | | | | |
| (D.3. Hopeless) | | | | | | | | |
| (A.1. LssMdReact) | | | | | | | | |
| (A.2. LeadParal) | | | | | | | | |
| (A.3. IpRjctSens) | | | | | | | | |

| 30 | | | | | | | |
|---|---|---|---|---|---|---|---|
| Date Elicited | | | | | | | |
| 1. Depress. | | | Depression | | | | |
| 2. Anxiety | | | Anxiety | | | | |
| 3. ApptDist. | | | Appetite Disturbance | | | | |
| 4a.. Slp. Dist. | | | Sleep Disturbance | | | | |
| 4b. Slp H/24 | | | Hours of Sleep Per 24 Hours | | | | |
| 4c. Slp Char. | | | Sleep Characteristics | | | | |
| 4d. MCA/7 | | | Mid-Cycle Awakenings | | | | |
| EMA/7 | | | Early Morning Awakenings | | | | |
| 5. Disint. | | | Disinterest | | | | |
| 6. Anhedonia | | | Anhedonia | | | | |
| 7. Libido | | | Libido Disturbance | | | | |
| 8. Energy | | | Energy Disturbance | | | | |
| 9. Thk/Conc. | | | Interference with Thinking or Concentration | | | | |
| 10. W.S.-B.G. | | | Feelings of Worthlessness, Self-Blame, or Guilt | | | | |
| 11. Death | | | Death Thoughts | | | | |
| 12. Suicide | | | Suicide Thoughts | | | | |
| 13. SHPI | | | Suicidal or Homicidal Plan or Intent | | | | |
| 14. N vs T | | | Nervousness versus Tiredness | | | | |
| | | | | | | | |
| 15. PsyTrop. | | | Psychotropic Medications | | | | |
| (mg/day) | | | (milligrams per day) | | | | |
| | | | | | | | |
| 16. OtherMeds | | | Other Medications | | | | |
| | | | | | | | |
| 17. Side Effs. | | | Side Effects (of Psychotropic Medications) | | | | |
| | | | | | | | |
| 18. Context | | | Events, Stressors, Pressures, etc. which effect mood | | | | |
| | | | | | | | |
| 19. ?'s/Loose Ends | | | Differential Diagnostic Questions, Unresolved Issues, ? Contradicitions ? | | | | |
| (Use OPTIONAL Clusters below only if these syndromes are suspected or diagnosed) | | | | | | | |
| (D.1. LwSlfEstm) | | | Low Self Esteem | | | Dysthymia Cluster | |
| (D.2. Indecision) | | | Indecision | | | | |
| (D.3. Hopeless) | | | Hopelessness | | | | |
| (A.1. LssMdReact) | | | Loss of Mood Reactivity | | | Atypical Cluster | |
| (A.2. LeadParal) | | | Leaden Paralysis | | | | |
| (A.3. IpRjctSens) | | | Interpersonal Rejection Sensitivity | | | | |

| Date Elicited | 06/04/xx | 07/05/xx | | | | | |
|---|---|---|---|---|---|---|---|
| 1. Depress. | 8 | 4 | | | | | |
| 2. Anxiety | 8 | 4 | | | | | |
| 3. ApptDist. | 8 | 4 | | | | | |
| 4a.. Slp. Dist. | 8 | 4 | | | | | |
| 4b. Slp H/24 | | | | | | | |
| 4c. Slp Char. | | | | | | | |
| 4d. MCA/7 | | | | | | | |
| EMA/7 | | | | | | | |
| 5. Disint. | 8 | 4 | | | | | |
| 6. Anhedonia | 8 | 4 | | | | | |
| 7. Libido | 8 | 4 | | | | | |
| 8. Energy | 8 | 4 | | | | | |
| 9. Thk/Conc. | 8 | 4 | | | | | |
| 10. W.S.-B.G. | 8 | 4 | | | | | |
| 11. Death | 8 | 4 | | | | | |
| 12. Suicide | 8 | 4 | | | | | |
| 13. SHPI | | | | | | | |
| 14. N vs T | | | | | | | |
| Total Score | 96 | 48 | | | | | |
| 15. PsyTrop. | | | | | | | |
| (mg/day) | | | | | | | |
| | | | | | | | |
| 16. OtherMeds | | | | | | | |
| | | | | | | | |
| 17. Side Effs. | | | | | | | |
| | | | | | | | |
| 18. Context | | | | | | | |
| | | | | | | | |
| 19. ?'s/Loose Ends | | | | | | | |
| (Use OPTIONAL Clusters below only if these syndromes are suspected or diagnosed) | | | | | | | |
| (D.1. LwSlfEstm) | | | | | | | |
| (D.2. Indecision) | | | | | | | |
| (D.3. Hopeless) | | | | | | | |
| (A.1. LssMdReact) | | | | | | | |
| (A.2. LeadParal) | | | | | | | |
| (A.3. IpRjctSens) | | | | | | | |

| | | | | | | | |
|---|---|---|---|---|---|---|---|
| Date Elicited | | | | | | | |
| Despair Cluster | | | | | | | |
| 1. Emot. Pain | | | | | | | |
| 2. NeverGetBetter | | | | | | | |
| 3. Overwhelm | | | | | | | |
| 4. Hopeless | | | | | | | |
| 5. Fear | | | | | | | |
| Melancholia Cluster | | | | | | | |
| 6. Worse A.M. | | | | | | | |
| 7. Retard/Agit | | | | | | | |
| 8. Weight Loss | | | | | | | |
| 9. Exc./InapGuilt | | | | | | | |
| MCPF Cluster | | | | | | | |
| MCPF Delus: | | | | | | | |
| 10. Inadequacy | | | | | | | |
| 11. Guilt | | | | | | | |
| 12. Dis/Death | | | | | | | |
| 13. Nihilism | | | | | | | |
| 14. DsvPunish | | | | | | | |
| 15. Halluc | | | | | | | |
| MIPF Cluster | | | | | | | |
| 16. Persecut | | | | | | | |
| 17. Thtins/Brdcast | | | | | | | |
| 18. Control | | | | | | | |
| 19. Suspic | | | | | | | |
| 20. IdeasOfRef | | | | | | | |
| 21. Halluc | | | | | | | |
| 22. | | | | | | | |
| 23. | | | | | | | |
| 24. | | | | | | | |
| 25. PsychMeds | | | | | | | |
| (mg/day) | | | | | | | |
| (D.3. Hopeless) | | | | | | | |
| | | | | | | | |
| | | | | | | | |
| 26. Other Meds | | | | | | | |
| | | | | | | | |

| | | | | | | |
|---|---|---|---|---|---|---|
| Date Elicited | | | | | | |
| Despair Cluster | | | | | | |
| 1. Emot. Pain | 611 | | Emotional Pain | | | |
| 2. NeverGetBetter | 612 | | Feelings You will Never Get Better from the Depression | | | |
| 3. Overwhelm | 613 | | Feeling Overwhelmed | | | |
| 4. Hopeless | 614 | | Feelings of Hopelessness | | | |
| 5. Fear | 615 | | Fear | | | |
| Melancholia Cluster | | | | | | |
| 6. Worse A.M. | 621 | | Depression Regularly Worse in the Morning | | | |
| 7. Retard/Agit | 622 | | Marked Psychomotor Retardation or Agitation | | | |
| 8. Weight Loss | 623 | | Significant Weight Loss | | | |
| 9. Exc./InapGuilt | 624 | | Excessive or Inappropriate Guilt | | | |
| MCPF Cluster | | | | | | |
| MCPF Delus: | 631 | | Mood-Congruent Delusions | | | |
| 10. Inadequacy | 632 | | Delusions of Inadequacy | | | |
| 11. Guilt | 633 | | Delusions of Guilt | | | |
| 12. Dis/Death | 634 | | Delusions of Death or Disease | | | |
| 13. Nihilism | 635 | | Nihilistic Delusions | | | |
| 14. DsvPunish | 636 | | Delusions of Deserved Punishment | | | |
| 15. Halluc | 637 | | Hallucinations | | | |
| MIPF Cluster | | | | | | |
| MIPF Delus: | 641 | | Mood-Incongruent Delusions | | | |
| 16. Persecut | 642 | | Delusions of Persecution | | | |
| 17. Thtins/Brdcast | 643 | | Thought Insertion/Thought Broadcasting | | | |
| 18. Control | 644 | | Delusions of Control | | | |
| 19. Suspic | 645 | | Suspicipusness | | | |
| 20. IdeasOfRef | 646 | | Ideas of Reference | | | |
| 21. Halluc | 647 | | Hallucinations | | | |
| 22. | | | | | | |
| 23. | | | | | | |
| 24. | | | | | | |
| 25. PsychMeds | | | Psychotropic Medications | | | |
| (mg/day) | | | (milligrams per day) | | | |
| | | | | | | |
| 26. Other Meds | | | Other Medications | | | |

Fig. 6

METHOD OF DIAGNOSING, TRACKING, AND TREATING DEPRESSION

TECHNICAL FIELD

The present invention relates generally to a method of psychiatric treatment, and in particular to tracking and rating depressive symptoms in a rapid, meaningful, and quantitative comparable way for treatment.

BACKGROUND OF THE INVENTION

Cost effectiveness has always been emphasized in the healthcare industry. With an estimated of $44 billion spent annually in the US to treat depression while only 6% of the health insurance policies provide outpatient benefits for psychiatric disorders, cost effectiveness is even more urgent in the psychiatric field.

Many rating scales measuring symptoms of mental disorders and depressions have been developed over the years in order to achieve cost effectiveness in the psychiatric field. These rating scales act as check-lists for clinicians and diagnosticians, monitoring patients' responses to certain treatments or reactions to environmental changes. These rating scales generally adopt a verbal symptom description method, relying on patients to verbally describe their feelings or elect from one of the verbally-described scenarios to match their feelings. Then, these rating scales rely on clinicians or diagnosticians to 'rate' the patients based on patients' responses.

Rating scales today can generally be classified into four groups: (1) for normal healthy individuals; (2) for assessing the social adjustments of patients in hospital wards; (3) for assessing patients' behaviors in hospital wards; and (4) for rating symptoms of mental illness. These ratings scales, although quite useful, have many limitations and shortcomings.

First of all, these rating scales often require verbal symptom communications, proving difficult or even impossible for alexithymic patients, trauma victims such as patients with post-traumatic stress disorder (PTSD), and patients who grew up in alcoholic or other dysfunctional families. These patients either are unable to communicate verbally, or they tend to suppress, repress, deny, or minimize their distress. These suppression mechanisms, often unconscious, may have been or may be very adaptive, ever since the patients' childhood environments. Due to these mechanisms, the verbal descriptions such patients give often lead clinicians and diagnosticians to under-diagnose their depression. Ultimately, poor treatment outcomes with relapses, or recurrences are inevitable.

Additionally, some patients might not be able to differentiate meanings between different medical terms, or they may consider themselves as treatment-resistant. Thus, eliciting verbal symptom descriptions directly from these patients often result in discrepancies and/or incorrect treatments.

Treatments for intense emotional pain, including depression subtypes and major depression with psychotic features such as mood-congruent psychotic features, mood-incongruent psychotic features, and melancholia differ significantly from treatments for uncomplicated major depressions. Thus, it is desirable to have a rating scale covering a whole range of symptoms in order to provide focused diagnosis and treatment.

However, rating scales devised specifically for rating symptoms of mental illness often cannot cover the whole range of symptoms. Even when the whole range of symptoms are covered, there are always difficulties with differentiating symptoms. This is due to the difficulty of differentiating or even defining some symptoms. For example, the term "delusion" may refer to grandiose, depressive, somatic, or even paranoid delusions which are quite different from one another and appear in different settings. Thus, after utilizing these rating scales, clinicians and diagnosticians are often left with an all-inclusive but messy, uninterpretable rating scale, or a rating scale not right-on-the-target of the patients' symptoms.

Furthermore, these rating scales usually are only devised for use on a special group of individuals. Thus, a pre-screening or a pre-diagnosis is often required prior to utilization of these scales. For example, ratings scales for normal healthy individuals do not screen for many mental disorder symptoms. In addition, such scales do not qualitatively distinguish between symptoms of mental illness and normal variations of behavior. As a result, over-diagnosis and thus over-treatment or more often the case, under-diagnosis and thus under-treatment occurs frequently.

Because these rating scales require the clinicians and diagnosticians to 'rate' the patients rather than self-assessments by the patients, oftentimes, ratings amongst different clinicians and diagnosticians result in wide discrepancies. Furthermore, when the rating scales are administered by only one clinician or diagnostician, these rating scales often are biased and thus, require some scaling or redistribution which are mere statistical estimations to correct such bias.

Even when these scales are designed for self-rating, literacy and minimal legal capacity are often required. Semiliterate patients often can not utilize these self-rating scales, and seriously ill patients may not have the mental capacity or faculties to utilize such scales, either.

Accordingly, there is a need in the art for a rating scale which elicits a patient's mental health states via a non-verbal communication means directly from a patient. There is also a need in the art for quantifying these non-verbal responses in order to compare the results of successive treatment trials.

Additionally, there is a need in the art for a rating scale capable of detecting and quantifying intense emotional pain or pains including depression subtypes and major depressions with psychotic features such as mood-congruent psychotic features, mood-incongruent psychotic features, and melancholia. A rating scale is also needed to highlight situations where a substantial amount of effort should be devoted first in order to treat other illnesses.

Furthermore, there is a need in the art for a rating scale covering the whole range of depression symptoms while providing clinicians and physicians an interpretable diagnosis. In addition, there is a need in the art for a rating scale where literacy and minimal mental capacity are not required in order to use the rating scale, and bias utilizing the rating scale is minimized. Also there is a need in the art for a rating scale which can be self-administered and/or administered by a non-clinician.

SUMMARY OF THE INVENTION

The present invention relates to a method of diagnosing, tracking, and rating depressive symptoms in order to predict responses to specific treatments and guide further adjustments and interventions to treatments. The present invention permits rapid depressive symptom severity ratings when conventional or verbal symptom descriptions are difficult or impossible. The present invention further provides a means for detecting and quantifying intense emotional pain, including depression subtypes and major depressions with psychotic features. The present invention also provides a means of quantitative comparisons for the results of successive treatment trials.

In one embodiment, the present invention relates to a method for determining the existence or non-existence of depression in an individual, the method including the steps of: (A) asking the individual at least one question regarding at least one depressive criterion; (B) recording the individual's answer(s) to the at least one question; and (C) scoring the individual's answer(s) so as to determine the existence or non-existence of depression in the individual, wherein the questions are worded so as to elicit a verbal and/or non-verbal numerical response from 0 to 10 where 0 represents the non-existence of at least one depressive criterion and 10 represents the most severe manifestation of at least one depressive criterion.

In another embodiment, the present invention relates to a method for determining the existence or non-existence of depression in an individual, the method further including the steps of (D) asking the individual further pre-designed questions regarding certain depression clusters, patterns and/or subtypes; and (E) scoring the individual's answer so as to determine the subtype and severity of depression in the individual.

In another embodiment, the present invention relates to a method for determining the existence or non-existence of depression in an individual, the method including the steps of: (A) asking the individual at least one question regarding at least one depressive criterion which requires a numerical response; (B) recording the individual's numerical response(s) to the at least one question; (C) scoring the individual's answer(s) so as to determine the existence or non-existence of depression in the individual; and (D) repeating steps (A) through (C) at regular intervals so as to track an individual's progression or regression.

In another embodiment, the method further includes the additional step of: (E) devising a course of treatment based on the information gathered in steps (A)–(D).

In another embodiment, the method includes repeating steps (A)–(E) until complete or nearly-complete symptom clearing is achieved.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

DESCRIPTION OF THE PREFERRED EMBODIMENTS

The present invention elicits patients' mental health states via a non-verbal communication means, i.e., numbers elicited directly from patients. Patients are able to give these numbers much more quickly and freely since numbers are less censored and less disturbing (i.e. cause less distress) than corresponding verbal descriptions.

Via a one-page visual display, the present invention instantly shows distinctive symptoms suggesting specific subtypes and clusters responsive to specific interventions. The visual and numeric display also provides immediate outcome data and immediate feedback on the effectiveness or ineffectiveness of treatment interventions, thereby facilitating treating to complete symptom clearing. In other words, the vastly greater ease of symptom descriptions and recordings via numbers also enables clinicians or diagnosticians to elicit, record, and display tractable data on follow-up visits in less time than an average diagnosis session in a useful and trackable form.

The present invention also facilitates identification of specific symptom patterns which predict responses to specific treatments. On subsequent visits, the present invention displays a patient's response to these specific treatments, thereby guiding further adjustments and interventions.

The present invention also provides a means of detecting and quantifying intense emotional pain, including depression subtypes, e.g., major depression with melancholia and major depressions with psychotic features such as mood-congruent psychotic features and mood-incongruent psychotic features The present invention will now be described with reference to the drawings, wherein like reference numerals are used to refer to like elements throughout.

Figure 1:
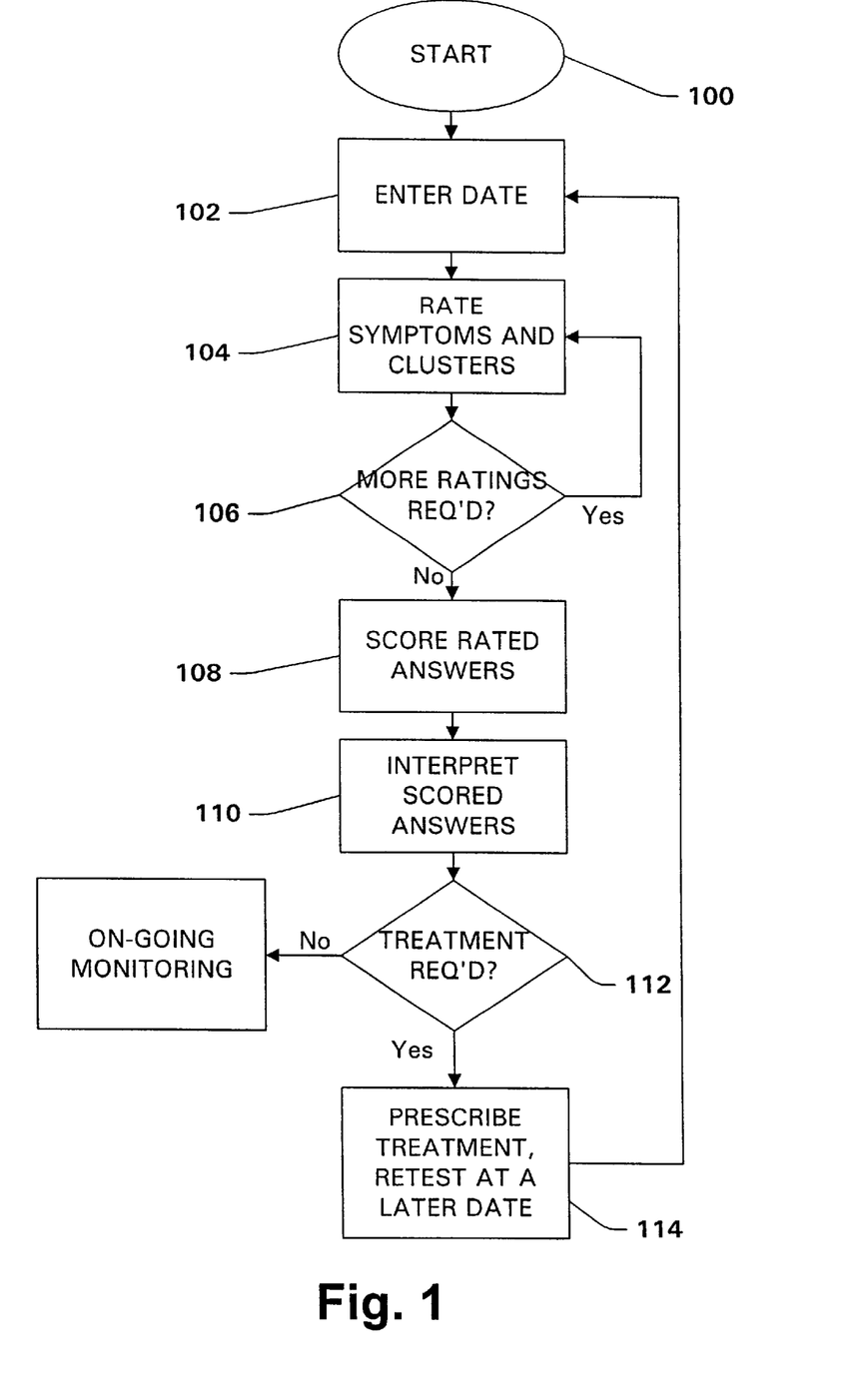
FIG. 1 is a flow chart illustrating a method of tracking and rating depressive symptoms in accordance with the present invention.
Figure 2:
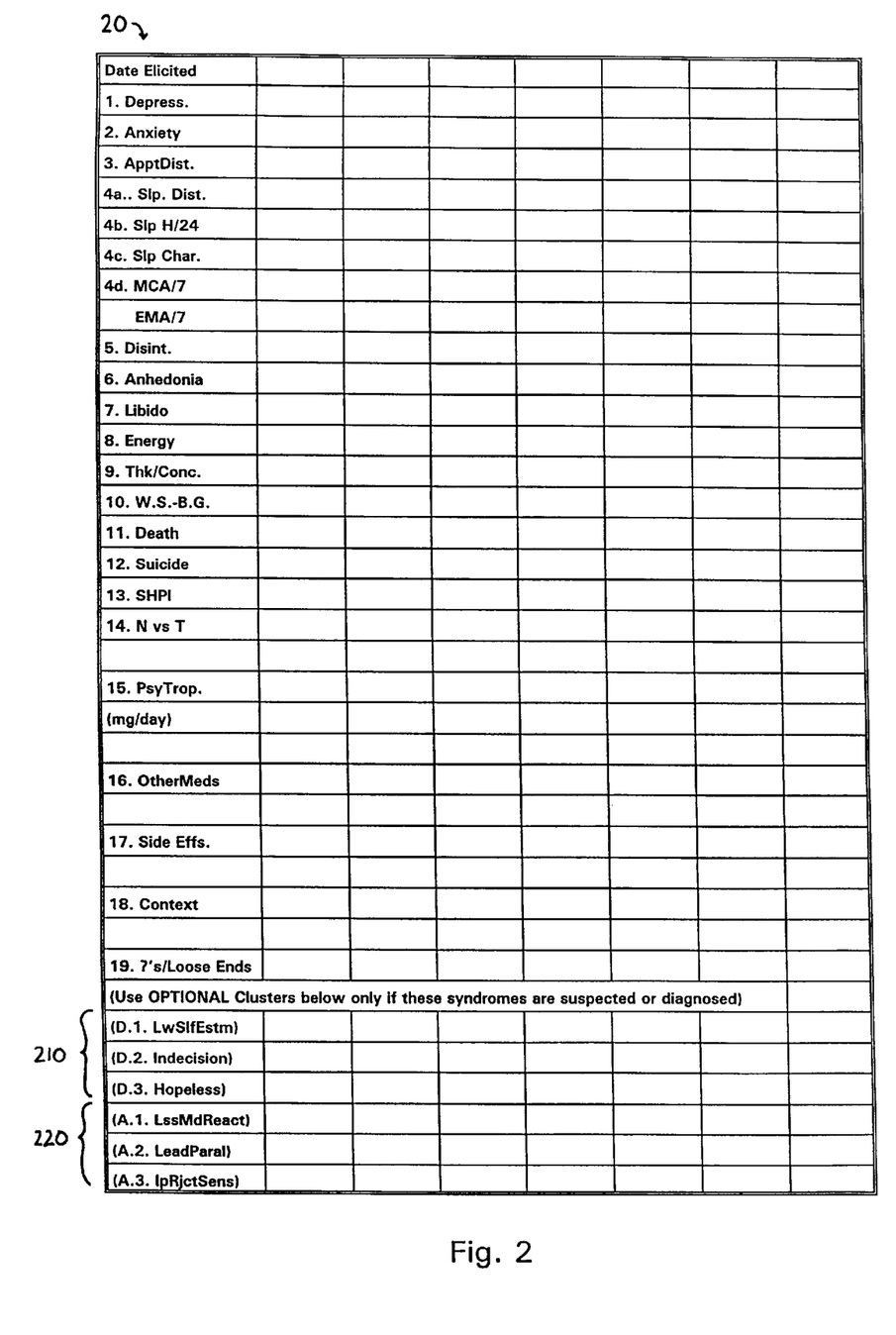
FIG. 2 is a diagnosis recording sheet 20 designed in accordance with the present invention.

Referring initially to FIG. 1, a flow chart illustrating a method of tracking and rating depressive symptoms in accordance with the present invention is shown. In step 100, a clinician or diagnostician may be seeing a patient for the first time or diagnosing the patient with the diagnosis recording sheet 20 for the first time. Since the diagnosis recording sheet 20 functions as a diagnosis sheet and a recording and tracking sheet, once a patient starts the recording process, the clinician and patient (in the situation where the method is clinician-administered) may utilize the recording sheet 20 to constantly monitor his or her progress. In addition, since the diagnosis recording sheet 20 may be utilized to prevent recurrences of depression, even after a patient's depressive symptoms are completely cleared, the patient and/or clinician may utilize the recording sheet 20 to continue monitoring the patient's condition to prevent relapses, or recurrences. Alternatively, a patient may use, by self-administration, diagnosis recording sheet 20 to track their own condition.

In step 102, the clinician enters the date of the diagnosis on a row designated on the diagnosis recording sheet 20. Dates are important for tracking length of treatment. In addition, dates may provide references to the effectiveness of a certain treatment or treatments. Thus, it is crucial for a clinician to record the dates when the symptoms are being elicited.

In step 104, the clinician asks a pre-designed question to elicit a numeric rating from the patient. Each question is designed to target a depressive diagnostic criterion and to elicit a numeric (or numerical) rather than verbal response. For example, to elicit a rating on depression, the clinician may ask, "on average for the past seven days up to right now, how severe would you say your discouragement and/or depression have been, with 10 being the worst possible and 0 being none at all?" Once the patient provides a numeric rating, the rating is immediately jotted down in the corresponding cell on the diagnostic recording sheet 20 in the column under the date elicited.

The clinician may develop a consistent and interpretable recording method to facilitate tracking of patient's symptoms. For example, if the patient gives a 2-number range for the symptom, e.g., "7 to 8", the clinician may always record the higher or the lower number for consistency.

The numerical rating method has several advantages over conventional verbal symptom description method. Initially, the numerical rating method enables the clinician to identify specific symptom patterns, prescribe treatments according to the patterns, and on subsequent visits, make adjustments to treatments. In addition, the numerical rating method permits rapid and meaningful quantification of depressive symptom severity for patients with verbal difficulties or impossibilities such as alexithymic patients, trauma victims with post-traumatic stress disorder (PTSD), and patients who may have grown up in alcoholic or other dysfunctional families.

The clinician will continue to elicit ratings on every depressive diagnostic criteria listed on the diagnostic recording sheet 20 and repeat steps 104 and 106 until no depressive symptoms or clusters remain un-rated on the recording sheet 20. Once all the symptoms and clusters on the diagnostic recording sheet(s) 20 are rated by the patient, the clinician proceeds to steps 108 and 110 to score and interpret the rated answers.

Since the symptom categories on the diagnosis recording sheet 20 were chosen to coincide with standard diagnostic criteria for depressive conditions such as the DSM-IV, 4th Edition, categories of the Diagnostic and Statistical Manual of the American Psychiatric Association, which is hereby incorporated by reference in its entirety. For the sake of brevity, the selection of the criteria and criteria's functions are not discussed in detail here. In addition, when interpreting the diagnosis recording sheet 20, DSM-IV standard or similar standards should be utilized. For example, five scores of 5 or greater on severity, including a depression score of 5 or greater, or a disinterest or anhedonia score of 7 or greater, would suggest a probable DSM-IV major depressive episode.

If a depressive pattern is identified in step 110, the clinician determines whether treatments are required in step 112. Treatments should typically be required until most, if not all, depressive symptoms reach the 0–2 range. This is due to the fact that sometimes, some patients may consider themselves treatment-resistant and thereby do not anticipate a complete or nearly-complete recovery.

Other times, patients may have experienced depressions for as long as they can remember, viewing these symptoms simply as who they are or as part of their personality. When patients underrate their symptoms, they will likely suffer further morbidity and limitations due to incompletely treated depression. In other words, failure to treat to complete symptomatic clearing leaves the patients vulnerable to relapses, recurrences, despairs, and/or suicides. Accordingly, treatments are necessary until complete or nearly-complete symptomatic clearing.

That is, complete recovery is evidenced when most, if not all, depressive symptoms reach 0, whereas nearly-complete recovery is evidenced when most, if not all, depressive symptoms are 2 or less.

Returning now to FIG. 1, in step 114, the clinician prescribes treatments as needed. Then, a subsequent visit should be scheduled where steps 102 to 114 are re-administered. Alternatively, if no treatments are required, the clinician will determine whether the target of complete or nearly-complete symptomatic clearing has been met.

Sometimes, the clinician may prescribe no treatment or no additional treatment where complete or nearly-complete symptomatic clearing is not achieved. This may be due to the need for further observations. The clinician should record such decisions on the diagnostic recording sheet 20, and a subsequent visit should still be scheduled as a follow-up. Alternatively, on-going monitoring may be need.

On the other hand, if the clinician determines that complete or nearly-complete symptomatic clearing is achieved, the patient may receive a diagnosis recording sheet 20 to self-monitor his/her own progress to prevent relapses or recurrences. The patient receives special instructions to follow steps 102 to 108, and if the scores and/or ratings ever rise above a predetermined level, a visit should be scheduled again.

Turning now to FIG. 2, a diagnosis recording sheet 20 designed in accordance with the present invention is shown. The diagnosis recording sheet 20 comprises of a table consisting of several cells made from several rows and columns. The intersection of a column and a row makes up a cell. Column 1 consists a list of preprinted shorthand annotations such as date of diagnosis and different depression symptoms. Column 2 is reserved for any potential retrospective entries, carefully labeled as such. Column 3 and all other rightward columns are blank columns for clinicians to record dates and symptoms elicited.

Figure 3A:
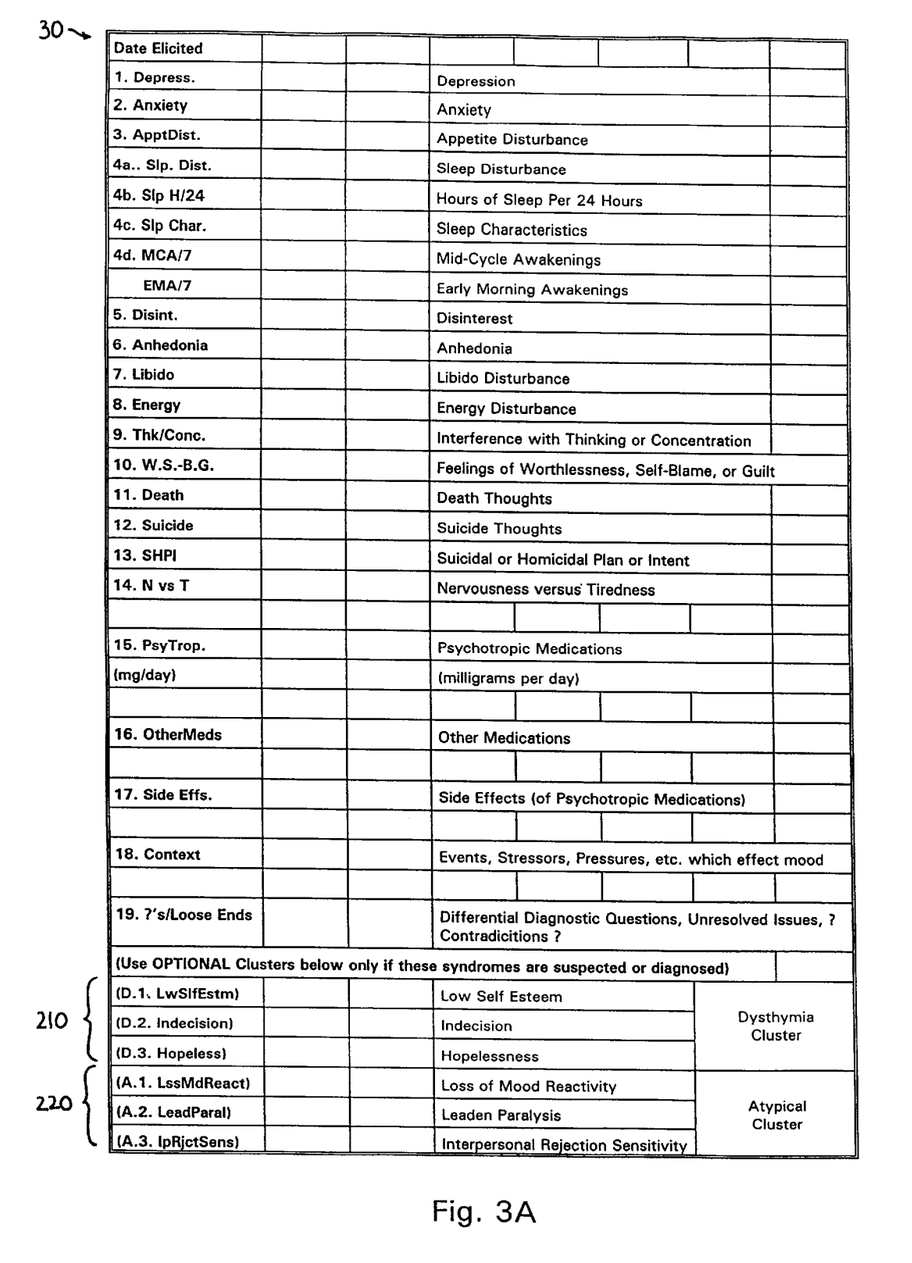
FIG. 3A is an annotated diagnosis recording sheet 30 designed in accordance with the present invention.
Figure 3B:
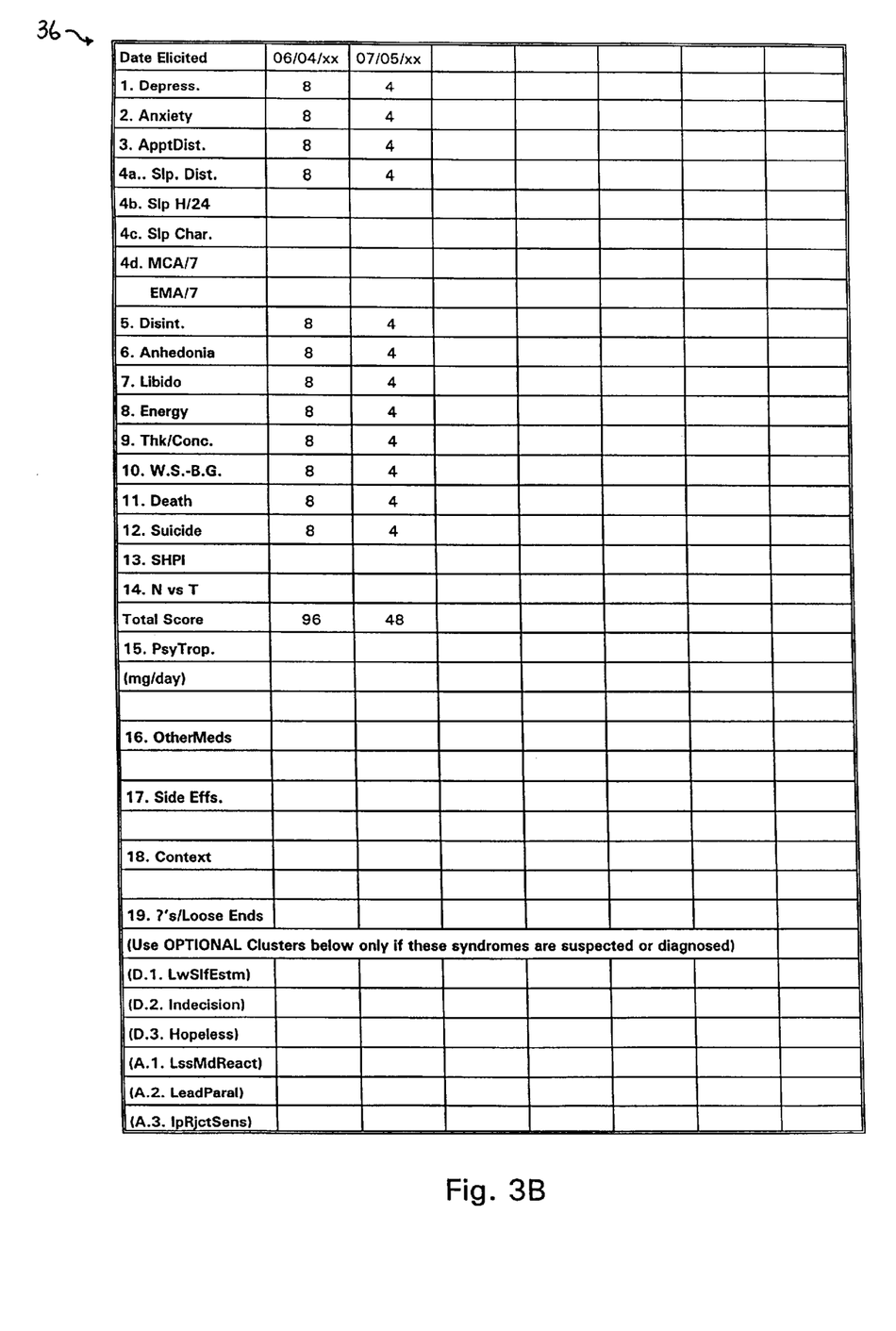
FIG. 3B is an un-annotated diagnosis recording sheet 36 designed in accordance with the present invention which depicts responses from two sessions with a patient.

The symptom categories illustrated on the diagnosis recording sheet 20 coincide with standard diagnostic criteria for depression such as the DSM-IV categories of the Diagnostic and Statistical Manual of the American Psychiatric Association, 4th Edition (DSM-IV). These standard diagnostic criteria include but are not limited to depression; anxiety; appetite disturbance; sleep disturbance; hours sleep per 24 hours; sleep characteristics; mid-cycle awakenings; early morning awakenings; disinterest; anhedonia; libido disturbance; energy disturbance; interference with thinking or concentrating; feelings of worthlessness, self-blame, or guilt; death thoughts; suicide thoughts; suicidal or homicidal plan or intent; nervousness vs. tiredness; psychotropic medications; other medications; side effects; events, stressors, pressures, etc. which may affect mood; differential diagnostic questions, unresolved issues, seeming contradictions; low self esteem; indecision; hopelessness; loss of mood reactivity; leaden paralysis; and interpersonal rejection sensitivity. FIG. 3 discusses in greater detail characteristics of each symptom, and for the sake of brevity, such discussion is omitted here.

The preprinted shorthand annotations such as date of diagnosis and different depression symptoms in Column 1 may vary depending on the purpose of the diagnosis recording sheet 20. For example, the exemplary diagnosis recording sheet illustrated in FIG. 2 is designed for initial diagnosis purposes. Depressions in the mild, moderate or moderate-to-severe range may all be diagnosed on this initial diagnosis recording sheet 20. As a result, clusters and patterns are also included in Column 1 to diagnose potential syndromes.

For example, depressions in the mild to moderate range which do not reach the threshold of major depressive episodes as defined by DSM-IV are generally referred to as dysthymic disorder or minor depression. Although they are only in the mild to moderate range, they may nonetheless cause considerable distress, limitation, and relative disability. As a result, even though clinicians may also detect dysthymic disorder via depression (Item 1), poor appetite or overeating (Item 3), insomnia or hypersomnia (Item 4a to 4d), and low energy or fatigue (Item 8), a dysthymic cluster 210 including low self esteem (D.1), poor concentration or difficulty in making decisions (D.2), and feelings of hopelessness (D.3) are is also included on this initial diagnosis recording sheet 20. Thus, based on the response to Items 1–18 of diagnosis recording sheet 20, the clinician and/or patient may forego administering/self-administering the dysthymia and atypical clusters (210 and 220, respectively).

Once dysthymic disorder is diagnosed via a diagnosis recording sheet 20, proper treatments may be initiated. Reactions to treatments may also be recorded on the diagnosis recording sheet 20 over time in order to track the responses and effectiveness of treatment.

Non-psychotic anxious depression with insomnia may also be diagnosed via the diagnosis recording sheet 20. For example, when nervousness is greater than tiredness (Item 14), when the anxiety score is greater than or equal to the depression score (Items 1 and 2), or when prominent insomnia exists with or without significant mid-cycle insomnia and/or early morning awakening (Items 4a to 4d), non-psychotic anxious depression with insomnia might exist and treatments may be prescribed accordingly.

Non-psychotic lethargic, hypersomnic depression may also be diagnosed via the diagnosis recording sheet 20. For example, when tiredness is great than nervousness (Item 14), when the depression score is greater than the anxiety score (Items 1 and 2), existence of prominent anhedonia and disinterest (Items 5 and 6), significantly decreased energy (Item 8), and/or significant hypersomnia (Items 4a–4c), then non-psychotic lethargic, hypersomnic depression may exist and treatments may be prescribed accordingly.

Atypical depression, or DSM-IV criteria of hypersomnic, hyperphagic, lethargic depression, may also be diagnosed via the diagnosis recording sheet 20. In addition to the atypical cluster, significant increase in appetite or weight gain (Item 3) or hypersomnia (Item 4a to 4c) may also assist with the diagnosis.

All of the core items on the diagnosis recording sheet 20 (i.e. Items 1–18 inclusive) should be elicited on every meeting. Such habit results in a well-documented diagnosis recording sheet 20 tracking patients' responses to each specific treatment instituted. In the event a patient's response is less than optimal (i.e., a non-complete symptomatic remission), the pattern of the responses shown on the diagnosis recording sheet 20 may provide useful hints to a clinician determining new treatments. Alternatively, a patient/clinician/non-clinician may decide to elicit less than all 18 core items from diagnosis recording sheet 20.

Specifically, in one embodiment the pre-designed questions asked by the clinician can be identical to or similar to those listed below, with the numerical responses thereto being immediately jotted down the clinician in the corresponding cell, based on Item number, on, for example, diagnostic recording sheet 20.

Item 1: On average for the past seven days up to right now, how severe would you say your discouragement and/or depression been with 10 being the worst possible and 0 being none at all?

Item 2. On average for the past seven days up to right now, how severe would say your nervousness and/or anxiety has been, with 10 being the worst possible and 0 being none at all?

Item 3. How much appetite disturbance have you had on average over the past seven days, with 10 being the worst and 0 being no disturbance? If the patient answers that there has been some degree of appetite disturbance, then the clinician should follow up with additional questions designed to elicit responses which help to clarify the type of appetite disturbance. For example, a clinician could inquire: Has your appetite been too much, too little, or up and down? Based on the patient's response the clinician should note to the right of the numerical answer given previously a symbol indicative of the patient's answer to the follow up question. For example, an up arrow can be used to signify that the patient's appetite has been too much, a down arrow for too little, and an up arrow coupled with a down arrow for signifying an up and down (i.e. a fluctuating) appetite.

Item 4a. How much sleep disturbance would you say you have had on average over the past seven days, with 10 being the worst and 0 being no sleep disturbance at all?

Item 4b. How many hours sleep per night have you been getting during the past week? OR What range of hours of sleep per night? The notation recorded in diagnostic recording sheet 20 can be, for example, 5/24 (meaning 5 hours of sleep per 24 hours) or (3–6)/24. If a patient reports also regularly taking a 2-hour daytime nap, this can be noted as follows: 5+2/24 or (3–6)+2/24. Also, the clinician should elicit a patient's average hours of sleep prior to the onset of depression, and record this next to the symptom description in the left column (Sleep: Hours/24).

Item 4c. Optionally, the clinician may ask any of the following questions which provided further clarifying information based on verbal responses given by a patient.

TABLE 1

| Question | Notation (Meaning) |
| --- | --- |
| Do you have trouble falling asleep? | i.i. (initial insomnia) |
| Do you have multiple brief (less than 1 hour each) awakenings during the night? | MBMCA (multiple brief mid-cycle awakenings) |
| Do you have poor sleep quality or wake up not feeling rested? | Qual. (quality) |
| Are your days and nights reversed?, i.e. Are you up most of the night and asleep most of the day? | D-NR (day-night reversal) |

Item 4d.1. Mid-cycle awakenings (MCA/7): How many (if any) of the past seven nights have you been awakened in the middle of the night (e.g. between midnight and 3 a.m.) and couldn't fall back asleep for an hour or more? An answer to such a question might be, for example, "2 nights", which would be noted as follows: 2/7.

Item 4d.2. Early morning awakenings (EMA/7): How many (if any) of the past seven mornings have you been awakened in the early morning (e.g. between 3 a.m. and 7 a.m.) and couldn't fall back to sleep for an hour or more? An answer to such a question might be, for example, "4 mornings", which would be noted as 4/7.

Item 5. On average during the past seven days how much interference have you had with your interests, with 10 being the worst and 0 being no interference?

Item 6. On average during the past seven days, how much interference have you had with your ability to experience pleasure, with 10 indicating complete interference with your ability to experience any pleasure, and 0 indicating no interference at all?

Item 7. On average during the past seven days, how much interference have you had with your sex drive, with 10 being total interference and 0 being no disturbance at all?

Item 8. During the past seven days how much disturbance have you had, on average, with your energy, with 10 being total interference and 0 being no disturbance at all? Energy disturbance may also be further qualified, as to type, in a manner similar to that discussed above with reference to Item 3.

Item 9. On average during the past seven days, how much interference have you experienced with thinking and/or concentrating, with 10 indicating total incapacitation, and 0 indicating no interference at all?

Item 10. During the past seven days on average how strong have your feelings of worthlessness, self-blame, and guilt been, on a scale of 0 to 10 , with 0 being no strong feelings of worthlessness, self-blame, and guilt and 10 nearly continuous strong feelings of worthlessness, self-blame, and guilt?

Item 11. On average during the past seven days, how strong have your thoughts of death been, with 10 indicating that death has been your only topic of thought and 0 indicating that you haven't thought about death at all?

Item 12. On average during the past seven days how strong have your thoughts of suicide been, with 10 being the maximum and 0 being none at all?

Item 13. Are you currently (right at this moment) planning or intending suicide or homicide? If the patient answers yes a workable safety plan must be designed with the patient and/or with others. If no, the clinician should note "Denies SHPI" (suicidal or homicidal plan or intent) in the appropriate space of the diagnostic recording sheet 20.

Item 14. Would you say that during the past seven days you have been, on average, more nervous, more tired, or "50–50"? Based on the answer given by the patient the clinician should jot down an appropriate notation on the diagnostic recording sheet 20. Some examples of appropriate notations are shown below in Table 2.

TABLE 2

| Choices | Notation |
| --- | --- |
| Nervousness has been more than tiredness | N > T |
| Tiredness has been more than nervousness | T > N |
| Nervousness and tiredness have been equal | N = T |
| Nervousness and tiredness have been roughly equal | N ≈ T |
| Patient has been neither nervous nor tired | N̶ T̶ |

Item 15. Which psychotropic medications (or medications for depression, anxiety, fears, etc.) are you currently taking? And what doses? The clinician should record any answers in the appropriate space on diagnostic recording sheet 20.

Item 16. Which other medications are you taking and at what doses? Again, The clinician should record any answers in the appropriate space on diagnostic recording sheet 20.

Also, the clinician should record on diagnostic recording sheet 20 information regarding any possible drug interactions or possible effects of the other medication on the patient's depressive illness.

Item 17. Which possible medication side effects are you experiencing, and also rate the severity of any such side effects with 0 indicating no severity and 10 indicating extreme severity?

Item 18. What has been going on in your life that may have an effect on your depression? The clinician records the verbal responses to this question in the appropriate space on diagnostic recording sheet 20.

Item 19. If not previously elicited elsewhere, the clinician should screen for substance abuse; history of mania, hypomania, or other indications of bipolar disorder; schizophreniform symptoms; mood-incongruent psychotic symptoms; mood-congruent psychotic symptoms (see also Clusters, Patterns, and Subtypes below); and cognitive impairment and/or other symptoms (e.g. visual or olfactory hallucinations) suggesting a possible medical or neurologic disorder as the cause of, or as a factor exacerbating, the patient's syndrome. If, after such screening, the primary working diagnosis remains depressive illness; but differential diagnostic questions, unresolved issues, or seeming contradictions remain, these may be recorded in Item 19.

In another embodiment, a patient may self-administer the pre-designed questions and note their numerical responses thereto on diagnosis recording sheet 20. The patient and/or the clinician may then use the patient's self-recorded numerical responses to track the patient's recovery and/or need for ongoing and/or additional and/or different treatments.

Turning now to FIG. 3, an annotated diagnosis sheet 30 designed in accordance with the present invention is shown. The annotated diagnosis sheet 30 has the same table structure with cells, rows, and columns as a non-annotated diagnosis recording sheet 20. However, rather than for recording and tracking, the annotated diagnosis sheet 30 provides short instructions to each depressive criterion. The annotated diagnosis sheet 30 may also act as an instruction sheet to be handed out to patients when they have achieved complete or nearly-complete symptomatic clearing and are in a maintenance phase. Additionally, the annotated diagnosis sheet 30 also provides for a quick reference to the diagnosis recording sheet 20.

For example, although Items 1 and 2 of the diagnosis recording sheet 20 may be easily understood to be referring to depression and anxiety, Item 3 "Appt Dist." may need clarification on the annotated diagnosis sheet 30. Item 3, "Appt Dist." stands for (or denotes) appetite disturbance.

Additionally, Item 4a "Slp Dist." refers to sleep disturbance while Item 4b "Slp H/24" refers to hours of sleep per night and also hours of sleep during the day (such as in the form of a nap or naps). Item 4c "Slp Char." (sleep characteristics) may be utilized to record any trouble the patient has falling asleep, multiple brief wakings during the night, poor sleep quality, waking up not feeling rested, or reversed days and nights.

Item 4d "MCA/7" is reserved for recording number of times in the past week the patient awakened in the middle of the night and could not fall back asleep for an hour or more. In addition, "EMA/7" refers to number of times in the past week the patient awakened in the early morning, for example, between 3 am and 7 am, and could not fall back asleep for an hour or more.

Item 5 "Disint." refers to interference with interests, and Item 6 "Anhedonia" refers to interference with ability to experience pleasure.

Item 7 "Libido" refers to interference with sex drive.

Item 8 "Energy" refers to disturbance with energy.

Item 9 "Thk/Conc" denotes interference with thinking or concentrating, and

Item 10 "W.S-B.G" denotes feelings of worthlessness, self-blame, and guilt.

Item 11 "Death" refers to patient's thoughts of death which are different from thoughts of suicide denoted by Item 12 "Suicide" or Item 13 "SHPI" suicidal or homicidal plan or intent.

Item 14 "N vs T" is a comparison between nervousness and tiredness.

Item 15 "PsyTrop" is reserved for psychotropic medications or any medications for depression, anxiety, fears, etc., and Item 16 "OthrMeds" is reserved for specifying any other medication prescribed/taken by the patient (i.e. medications unrelated to the treatment of psychological/psychiatric disorders/conditions (i.e. mental disorders)). This item can be useful in avoiding drug complications/side effects/ interactions.

Item 17 "SideEff" refers to possible medication side effects or allergies.

Item 18 "Context" would record any other events or factors that the patient or diagnostician believes to affect a patient's depression. For example, situations such as getting laid off, death of or separation from a patient's significant other, family members, or friends, home or work pressures, or any substance use/abuse may all influence the patient's depression.

Item 19 "?'s.LooseEnds" is reserved for history of substance abuse, mania, hypomania, or other indications of a possible bipolar disorder, schizophreniform symptoms, mood-incongruent psychotic symptoms, mood-congruent psychotic symptoms, cognitive impairments, or visual or olfactory hallucinations, or other unresolved differential diagnostic questions.

Furthermore, D.1 LwSlfEstm or low self esteem, D.2 Indecision, and D.3 Hopeless make up the dysthymic cluster 210 discussed above, and A.1 LssMdReact or loss of mood reactivity, A.2 LeadParal or leaden paralysis, and A.3 IpRjct-Sens or interpersonal rejection sensitivity make up the atypical cluster 220 discussed above.

Severe depressive conditions are often associated with intense emotional pain and serious interference with the ability to function. They often are associated with an increased risk of suicide, and specific therapies and treatments need to be delineated in order for speedy recovery. Accordingly, a diagnosis recording sheet 20 designed for initial diagnosis and tracking may be insufficient for patients suffering from severe depression or depressive episodes. In such a case, a severe depression diagnosis recording sheet 50 as shown in FIG. 5 should be utilized.

Figure 4:
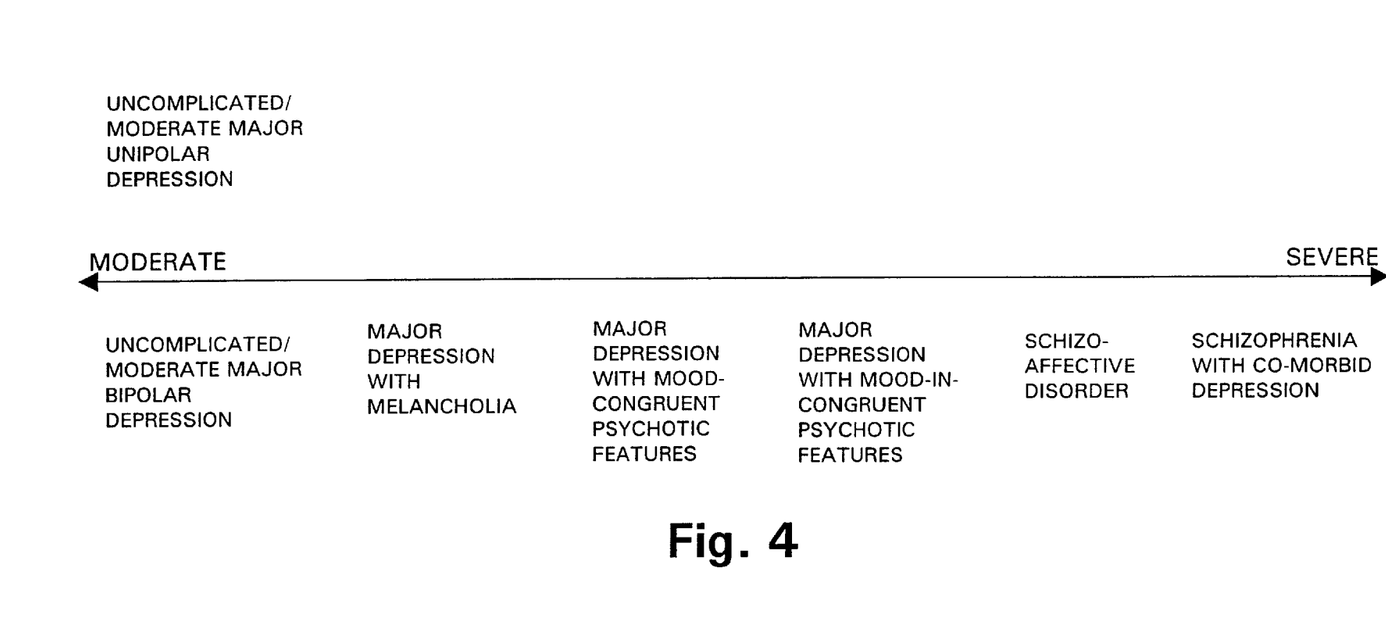
FIG. 4 is a graph illustrating a continuum between moderate to severe types of depressions.

Generally, moderate, moderate-to-severe, and severe depression may be thought of as lying along a continuum as illustrated by FIG. 4. Severity generally increases from left to right, as indicated in FIG. 4, with uncomplicated unipolar and bipolar depression being less severe in comparison to various subtypes of depression in the middle and schizophrenia with co-morbid depression at the extreme. Other than non-severe uncomplicated depression, symptoms may be severe and/or incapacitating with the presence of a suicide risk.

Figure 5:
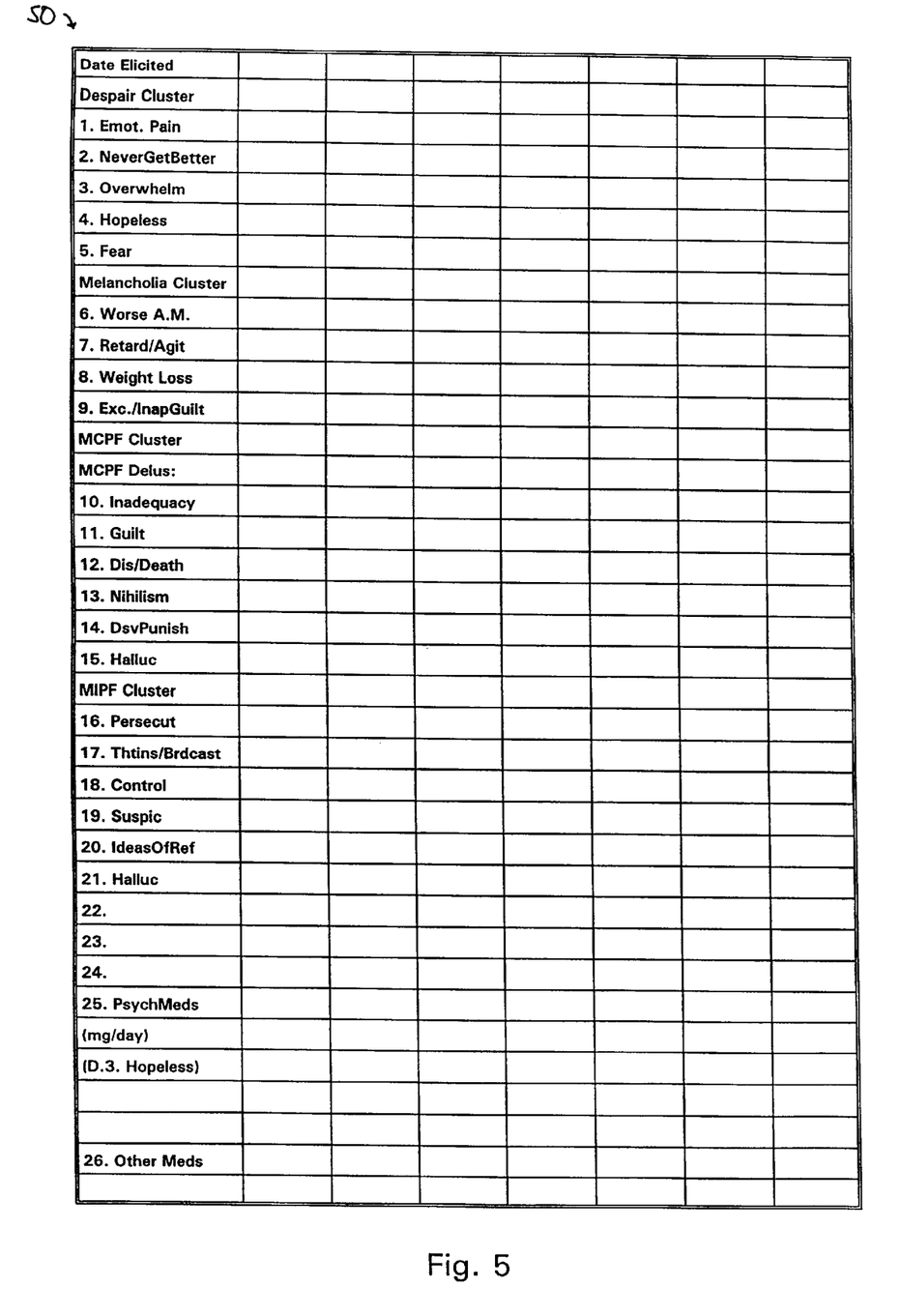
FIG. 5 is a severe depression diagnosis recording sheet 50 designed in accordance with the present invention.

Turning now to FIG. 5, a severe depression diagnosis recording sheet 50 is shown. Severe depression diagnosis recording sheet 50 is utilized when the scoring from diagnosis recording sheet 20 so dictates. For example, when the scoring of diagnosis recording sheet 20 contains five scores of 5 or greater, including a disinterest (Item 5) or anhedonia (Item 6) score of 7 or greater, or a depression score of 5 or greater (Item 1), this would/may suggest a probable DSM-IV major depressive episode. Thus, severe depression diagnosis sheet 50 is utilized by a clinician and/or patient to determine the possible type of depression a patient may be experiencing.

Specifically, similar to a diagnosis recording sheet 20, Row 1 of severe depression diagnosis recording sheet 50 is reserved for date entries, Column 1 consists a list of preprinted shorthand annotations, Column 2 is reserved for possible retrospective entries, and Column 3 and other rightward columns are blank columns for a clinician and/or patient to record dates and symptoms elicited.

The severe depression diagnosis recording sheet 50 gauges the magnitude of severe depressions and aids in the differentiation of severe depression subtypes. The severe depression diagnosis recording sheet 50 also tracks a patient's response to treatment and facilitates treating to the point of complete symptomatic clearing. Like the diagnosis recording sheet 20, the severe depression diagnosis recording sheet 50 only elicits numeric ratings or responses from patients including, but not limited to, alexithymic patients, trauma victims such as patients with post-traumatic stress disorder (PTSD), and patients who grew up in alcoholic or other dysfunctional families who usually have difficulties providing conventional verbal symptom descriptions. Accordingly, the present invention provides a means for proper depression diagnosis.

In addition to the categories lists in Column 1, the diagnosis recording sheet 20 and the severe depression diagnosis recording sheet 50 differ in another aspect. Rather than eliciting all of the core items on a regular basis as a diagnosis recording sheet 20 does, the severe depression diagnosis recording sheet 50 identifies only one or two severe depressive subtype(s) and tracks patient's response to the identified symptoms of the subtype(s).

The severe depression diagnosis recording sheet 50 may or may not be utilized on a patient's first visit. Such a determination (whether or not to administer or self-administer the diagnosis recording sheet 50) should generally be based upon the results ascertained from diagnosis recording sheet 20. However, a clinician and/or patient may administer the severe depression diagnosis recording sheet 50 based on their personal observations and/or experience. In a self-administered situation, the patient themselves may know based on personal experience that they are experiencing a "severe depressive episode" and thus that they should self-administer the severe depression diagnosis recording sheet 50.

When responses on the general diagnosis recording sheet 20 point to one or more severe depressive subtypes, the clinician (or patient) may then administer and refer to the severe depression diagnosis recording sheet 50 for specific tailored tracking.

For example, patients who, at any visit, report 4 or more symptoms on the general diagnosis recording sheet 20 of 8 or greater severity are then referred to the despair cluster of the severe depression diagnosis recording sheet 50.

Alternatively, if a patient reports symptoms scores of 7 or more on 3 or more of Items 2, 10, 11, or 12 of the general diagnosis recording sheet 20, e.g., anxiety, death thoughts, suicide thoughts, or feelings of worthlessness, self-blame, or guilt, or scores of 8 or more on 2 or more of these Items, the patient should also be referred to the severe depression diagnosis recording sheet 50 as he/she may have a very serious depression with some suicide risk.

A standard severe depression diagnosis recording sheet 50 identifies four clusters as diagnostic criteria including, but not limited, to the despair cluster comprising emotional pain, feelings of never getting better, feelings of being overwhelmed, feelings of hopelessness, and fear; the melancholia cluster comprising regular morning depressions, marked psychomotor retardation or agitation, significant weight loss, and excessive or inappropriate guilt; the mood-congruent psychotic features cluster comprising delusions of inadequacy, guilt, death, or disease, nihilistic delusions, delusions of deserving punishment, and hallucinations; and the mood-incongruent psychotic features cluster comprising delusions of persecution, thought insertion or thought broadcasting, delusions of control, suspiciousness, ideas of reference, and hallucinations. These clusters and subtypes cover the full range of DSM-IV clusters and subtypes in order to utilize all of the well-documented treatments tailored to DSM-IV depressive disorders. Other clusters and diagnostic criteria may be added as clinicians or diagnosticians deem appropriate.

Figure 6:
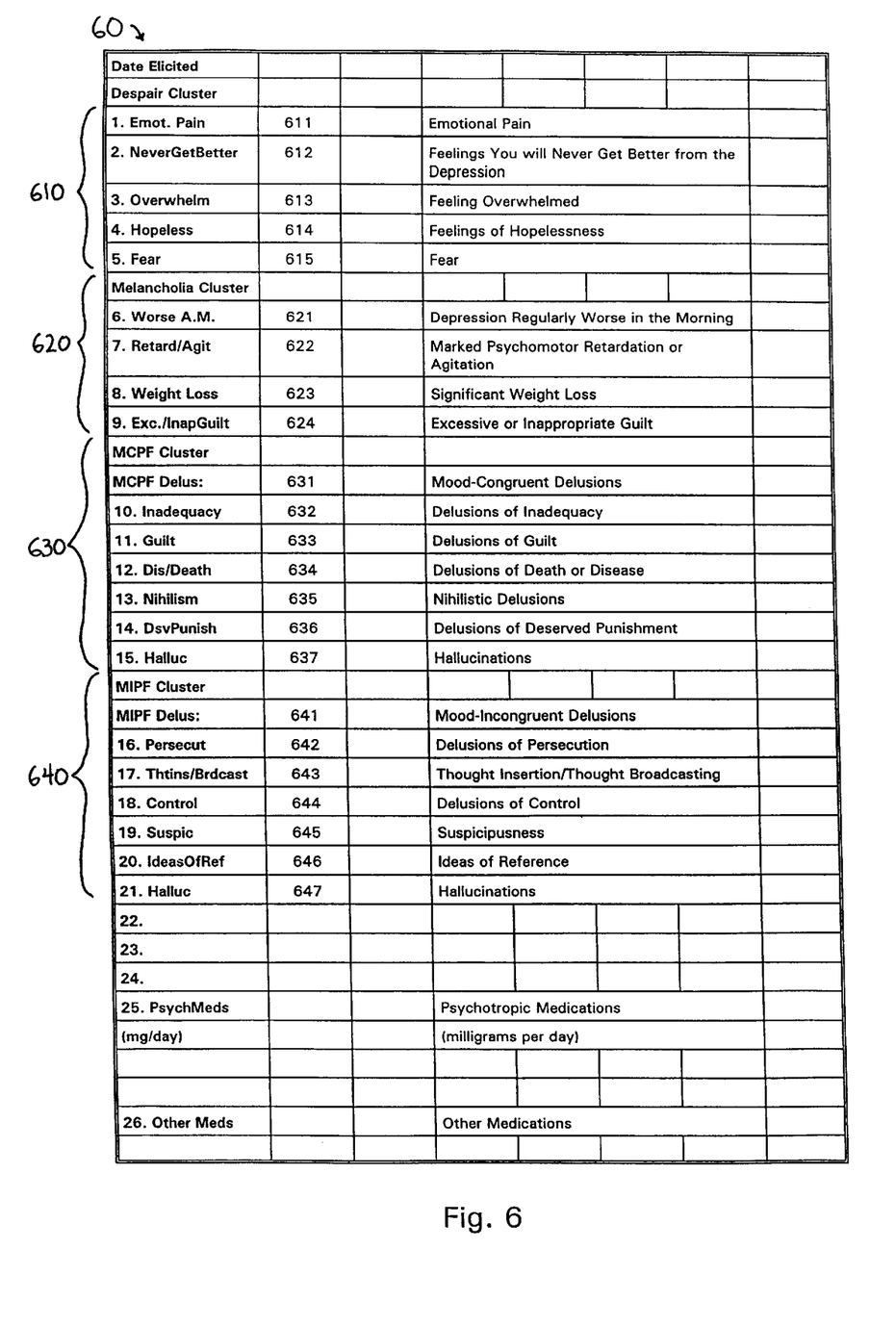
FIG. 6 is an annotated severe depression diagnosis recording sheet 60 designed in accordance with the present invention.

Turning to FIG. 6 now, an annotated severe depression diagnosis sheet 60 designed in accordance with the present invention is shown. The annotated severe depression diagnosis sheet 60 has the same table structure with cells, rows, and columns as a non-annotated severe depression diagnosis sheet 50. Additionally, similar to an annotated diagnosis sheet 30, an annotated severe depression diagnosis sheet 60 provides short instructions and acts as a quick reference for each depressive criterion on the non-annotated sheet 50.

The annotated severe depression diagnosis sheet 60 as shown in FIG. 6 comprises four clusters: (1) despair cluster 610; (2) melancholia cluster 620; (3) mood-congruent psychotic features cluster 630; and (4) mood-incongruent psychotic features cluster 640. The shorthand notations utilized on the severe depression diagnosis recording sheet 50 are explained on the annotated severe depression diagnosis sheet 60 as follows.

Despair Cluster 610 comprises Emot Pain 611 denoting emotional pain; NeverGetB 612 denoting feelings that the patient thinks that they will never get better from depression; Overwhelm 613 denoting feelings of being overwhelmed; Hopeless 614 denoting feelings of hopelessness; and Fear 615.

Melancholia Cluster 620 comprises WorseA.M. 621 denoting a regular occurrence of worse depression in the morning; Retard/Agit 622 denoting marked psychomotor retardation or agitation; WeightLoss 623 denoting significant weight loss; and Exc/InapGuilt 624 denoting excessive or inappropriate guilt.

MCPF Cluster 630 or mood-congruent psychotic features cluster comprises MCPF Delus 631 or mood-congruent psychotic feature delusions, including Inadequacy 632 or delusions of inadequacy; Guilt 633 or delusions of guilt; Dis/Death 634 or delusions of death or disease; Nihilism 635 or nihilistic delusions; and DsvPunish 636 or delusions of deserved punishment. MCPF Cluster 630 further comprises Halluc 637 or hallucinations.

MIPF Cluster 640 or mood-incongruent psychotic features cluster comprises MIPF Delus 641 or mood-incongruent psychotic feature delusions, including Persecut 642 or delusions of persecution; ThtIns/Bc 643 or thought insertion or thought broadcasting; and Control 644 or delusions of control. MIPF Cluster 640 further comprises Suspic. 645 or suspiciousness, IdsOfRef 646 or ideas of reference, and Halluc 647 or hallucinations.

Similar to general diagnosis recording sheets 20 and 30, rows are reserved for psychotropic medications and/or other medications in order to track the effectiveness of the treatments and to prevent drug complications. This item can also be useful in avoiding drug complications/side effects/interactions with medications unrelated to any psychological/psychiatric disorder.

Combining the general diagnosis recording sheet 20 and the severe depression diagnosis recording sheet 50, a clinician may diagnose moderate-to-severe or even severe depression along the continuum illustrated in FIG. 4. For example, due to its specific DSM-IV criteria and distinct treatment response patterns, major depression with melancholia may be identified when prominent anhedonia (severe depression diagnosis recording sheet 50, Item 6) or loss of mood reactivity to pleasurable stimuli (a score of 6 or more on the general diagnosis recording sheet 20, Atypical cluster 220, Item A.1) is combined with three or more of (1) a distinctly depressed mood (a score of 8 or more on the general diagnosis recording sheet 20, Item 1), (2) early morning awakening by two hours or more (general diagnosis recording sheet 20, Item 4d), (3) depression regularly worse in the morning (general diagnosis recording sheet 50, Item 6), (4) marked psychomotor retardation or agitation (severe depression diagnosis recording sheet 50, Item 7), (5) significant anorexia (general diagnosis recording sheet 20, Item 3) or weight loss (severe depression diagnosis recording sheet 50, Item 8), or (6) excessive or inappropriate guilt (severe depression diagnosis recording sheet 50, Item 9).

Major depression with mood-congruent psychotic features may also be identified when hallucinations, delusions, or distinct delusional tone with the typical depressive themes of personal inadequacy, guilt, disease, death, nihilism, or deserved punishment (severe depression diagnosis recording sheet 50, Items 10–15) are reported on the severe depression diagnosis recording sheet 50.

Major depression with mood-incongruent psychotic features or schizo-affective disorder and schizophrenia with depression may also be identified when prominent fears, suspiciousness, ideas of reference, hallucinations, or delusions are reported or exhibited spontaneously with or without the typical depressive themes of personal inadequacy, guilt, disease, death, nihilism, or deserved punishment (severe depression diagnosis recording sheet 50, Items 16–24).

The aforementioned method of diagnosing, tracking, and treating depression improves the efficiency of the classification, tracking, and management of the patient's depressive illness, and thereby frees up valuable time to explore and resolve difficult and conflicted issues in the patient's life, preventing these issues from further affecting the course of the patient's depressive illness. The present invention permits rapid and meaningful depressive symptom severity ratings when conventional or verbal symptom description is difficult or impossible. Via a one-page visual display, the present invention instantly shows distinctive symptoms suggesting specific subtypes and clusters responsive to specific interventions. The visual and numeric display also provides immediate outcome data and immediate feedback on the effectiveness or ineffectiveness of treatment interventions, thereby facilitating treatment to complete or nearly-complete symptom clearing.

Specifically, diagnostic recording sheets 20 and 50 seek to elicit information regarding certain types of depression clusters, patterns and/or subtypes. Examples of such depression clusters, patterns and/or subtypes will be discussed below in detail.

A. Depressions in the Mild. Moderate. and Moderate-to-Severe Range

1. Dysthymic Disorder:

This refers to depressions in the mild-to-moderate to moderate range which do not reach the threshold of major depressive episodes (see DSM-IV). They may nonetheless cause considerable distress, limitation, and relative disability. When recognized and treated tenaciously using the present inventive method, they can often be treated to complete symptomatic clearing. Such depressive episodes can be recognized by the following scoring features on diagnosis recording sheet 20.

a. Depression score (Item 1) of 5 or more for at least 2 years.

b. Presence while depressed of 2 or more of the following (severity of 4 or more):

1. Poor appetite or overeating (Item 3)

2. Insomnia or hypersomnia (Items 4a through 4d)

3. Low energy or fatigue (Item 8)

4. Low self esteem (Dysthymic Cluster Item D.1. Note: Dysthymic Cluster is on diagnosis recording sheet 20 below Item 19.)

5. Poor concentration (Item 9) or difficulty making decisions (Dysthymic Cluster Item D.2: Indecision)

6. Feelings of hopelessness (Dysthymic Cluster Item D.3)

c. The patient may report additional depressive symptoms, often in the 2 to 6 severity range.

2. Non-Psychotic Anxious Depression with Insomnia ("Nervous Depression"):

Such depressive episodes can be recognized by the following scoring features on diagnosis recording sheet 20.

a. Nervousness greater than tiredness (N>T, Item 14).

b. Anxiety score ≧ Depression score (often, Items 1 and 2).

c. Prominent Insomnia, often with significant mid-cycle insomnia (MCA/7) and/or early morning awakening (EMA/7) (Items 4a–4d).

3. Non-Psychotic Lethargic. Hypersomnic Depression ("Draggy Depression"):

Such depressive episodes can be recognized by the following scoring features on diagnosis recording sheet 20.

a. Tiredness greater than Nervousness (T>N, Item 14)

b. Depression score>Anxiety score (Items 1 and 2).

c. Prominent Anhedonia and Disinterest (Items 5 and 6).

d. Significantly (>6–10) decreased energy (Item 8).

e. Significant hyper-somnia is often present (Items 4a–4c).

f. Note: If the patient reports intact mood reactivity, heavy feelings in arms or legs, and/or interpersonal rejection sensitivity, consider the possibility of atypical depression.

4. Atypical Depression:

This refers to certain hypersomnic, hyperphagic, lethargic depressions with specific DSM-IV criteria and specific differential treatment responses. Such depressive episodes can be recognized by the following scoring features on diagnosis recording sheet 20.

a. Significant increase in appetite (Item 3) or significant weight gain.

b. Hyper-somnia (Items 4a–4d).

c. Intact mood reactivity (mood improves in reaction to favorable events, i.e. score of 4 or less on Atypical Cluster Item A.1, Loss of Mood Reactivity. Atypical Cluster on diagnosis recording sheet 20.

d. Leaden paralysis (heavy feelings in arms or legs—Atypical Cluster Item A.2).

e. Long-standing pattern of interpersonal rejection sensitivity (not limited to episodes of mood disturbance) resulting in significant social or occupational impairment (Atypical Cluster Item A.3).

5. Seasonal Affective Disorder (SAD):

This refers to patients which present a depressive state or a worse depressive state at about the same time each year. Often this is accompanied by "reverse"/atypical vegetive symptoms (e.g., hypersomnia and/or hyperphagia). The diagnosis recording sheet 20 will confirm SAD by showing a pattern of worsening during the same months each year. Thus, in order to diagnosis such a disorder, it is critical that a file for each patient be maintained so that their diagnosis recording sheets can be saved over a lengthy period of time (e.g., for at least 1 year or more). For most patients, morning light therapy has been shown to be an effective method of treating SAD.

Below in Table 3 is a comparison between "Nervous Presentations Depression" (see A.2 above), "Draggy Presentations" (see A.3 above) and "Cyclic Presentations".

TABLE 3

| Nervous Depression | Draggy Depression | Cyclic Presentations |
|---|---|---|
| Depression + anxiety disorder<br>a. Panic Disorder<br>b. Generalized Anxiety (GAD)<br>c. Obsessive-Compulsive Disorder (OCD)<br>d. Post-Traumatic Stress Disorder (PTSD)<br>Depression + Dissociative Disorder | Atypical Depression (see A.4 above) | With Long Cycles:<br>a. Classical Bipolar Disorder (see B.7 below)<br>b. Seasonal Affective Disorder (SAD) (see A.5 above)<br>With Short Cycles<br>a. Bipolar Disorder with Rapid Cycling (see B.7 below)<br>b. Premenstrual Dysphoric Disorder (PMDD)<br>c. Depression with Personality Disorder |
| Depression + Eating Disorder | Some Dysthymias | With Relatively Mild Cycles<br>a. Cyclothymia |
|  | Some "Double Depressions" (dysthmia + major depression)<br>Seasonal Affective Disorder (See A.5 above) | Bipolar Disorder NOS |
| Some Depressions with Melancholia<br>Depression + Psychosis<br>a. Depression + MCPF<br>b. Depression + MIPF<br>C. Schizoaffective Depression<br>d. Schizophrenia with Depression | Some Depressions with Melancholia<br>Some Depressions with Psychosis<br>a. Depression with mood-congruent psychotic features<br>b. Depression with mood- |  |

TABLE 3-continued

| Nervous Depression | Draggy Depression | Cyclic Presentations |
|---|---|---|
| | incongruent psychotic features | |
| | c. Schizoaffective Disorder, depressed | |
| | d. Schizophrenia with depression | |
| "Nervous Depression NOS" (see A.2 above) | "Draggy Depression NOS" (see A.3 above) | Cyclic Depression NOS |

B. Moderate-to-Severe and Severe Depression: Conceptualization and Classification/Subtypes Severe depression is often associated with intense emotional pain and serious interference with ability to function, and thereby carries an increased risk of suicide. Paradoxically, however, there is some indication that severe depressions may respond better than mild and moderate depressions to effective somatic therapies (pharmacotherapy or ECT).

As is discussed above, moderate, moderate-to-severe, and severe depressions may be thought of as lying along a continuum, with uncomplicated unipolar and bipolar depression at the left of the page, various subtypes in the middle, and schizophrenia with co-morbid depression at the far right (see FIG. 1). In general, severity increases from left to right, but anywhere to the right of non-severe uncomplicated depression, symptoms may be severe and/or incapacitating, and/or present a suicide risk.

Whereas diagnosis recording sheet 20 generally elicits all of the core items on a regular basis, severe depression diagnosis recording sheet 50 identifies one severe depressive subtype (or possibly two) during the course of evaluation, and tracks the response of the identified symptoms of the subtype (as well as the response of the Despair Cluster, if positive, through treatment to complete clearing.

For example, patients who, at any visit, report 4 or more symptoms on the diagnosis recording sheet 20 of 8 or greater severity (especially if these include anxiety, death thoughts, suicide thoughts, or feelings of worthlessness, self-blame, or guilt should be asked the Despair Cluster on severe depression diagnosis recording sheet 50, which includes the Items 1 through 4:

1. On average for the past seven days, how much emotional pain have you been feeling, with 10 being the worst possible, and 0 being no emotional pain?
2. During the past seven days, on average, how strong has your feeling been that you will never get better from the depression, 0 to 10, with 10 being the strongest?
3. How overwhelmed have you felt on average over the past seven days, 0 to 10, with 10 being completely overwhelmed?
4. How much hopelessness have you felt on average over the past seven days, 0 to 10, with 10 being complete hopelessness?
5. How much fear have you felt on average over the past seven days, 0 to 10?

If the patient reports symptom scores of, for example, 7 or more on 3 or more of the above items, or scores of 8 or more on 2 or more of the above items, this may represent a very serious depression with some suicide risk. Rapid and specific diagnosis and aggressive treatment are in order.

1. Mayor Depression with Melancholia:

Major depression with melancholia is a distinct severe depression subtype more common in patients over age 50, with very specific DSM-IV criteria and a distinct and relatively well-defined treatment response pattern. A number of hospital studies of major depression with melancholia have shown remission rates of only 25% to 50% to treatment with the selective serotonin re-uptake inhibitors (SSRI's), but remission rates of 50% to 75% with mixed-action anti-depressants (i.e., those affecting more than one neurotransmitter system) or noradrenergic antidepressants. As the SSRI's are by far the most widely prescribed anti-depressant class, the identification and differential treatment of major depression with melancholia takes on major significance.

Such depressive episodes can be recognized by the following scoring features on diagnosis recording sheet 20.

1. Prominent anhedonia (Item 6 of FIG. 2 (hereinafter FIG. 2 will be referred to as diagnosis recording sheet 20); or
2. Loss of mood reactivity to pleasurable stimuli (score of 6 or more on Atypical Cluster, Item A.1).

Plus three or more of the following:

3. Distinctly depressed mood (score of 8 or more on diagnosis recording sheet 20, Item 1);
4. Early morning awakening (at least 2 hours or more on diagnosis recording sheet 20, Items 4d);
5. Depression regularly worse in the morning (severe depression diagnosis recording sheet 50, Item 6);
6. Marked psychomotor retardation or agitation (severe depression diagnosis recording sheet 50, Item 7);
7. Significant anorexia (diagnosis recording sheet 20, Item 3) or weight loss (severe depression diagnosis recording sheet 50, Item 8); and
8. Excessive or inappropriate guilt (severe depression diagnosis recording sheet 50, Item 9)

2. Mayor Depression with Mood-Congruent Psychotic Features:

Such depressive episodes can be recognized by the following scoring features on diagnosis recording sheet 20. If the patient reports (or if the clinician elicits) hallucinations, delusions, or distinct delusional tone "with the typical depressive themes of personal inadequacy, guilt, disease, death, nihilism, or deserved punishment" (severe depression diagnosis recording sheet 50, Items 10–15), major depression with MCPF should be strongly suspected, and strong consideration should be given to the immediate institution of known effective treatment options.

3. Mayor Depression with Mood-Incongruent Psychotic Features:

Those patients with this type of depressive disorder may spontaneously report or exhibit prominent fears, suspiciousness, ideas of reference, hallucinations, or delusions. If not, the clinician must inquire about these as part of the mental status examination. If present they may be recorded on severe depression diagnosis recording sheet 50, Items 16 through 24. They may indicate MIPF, schizoaffective disorder, schizophrenia, or other psychotic disorder and the DSM-IV should be consulted to make these distinctions. If the diagnosis is major depression with MIPF, the patient's symptoms may be recorded in spaces for Items 16–24 of the severe depression diagnosis recording sheet 50. Items 16–24 are as follows:

16. Persecutory delusions;
17. Thought insertion/thought broadcasting;
18. Delusions of control;
19. How much suspiciousness have you experienced on average during the past week, 0 to 10, with 10 being the most possible?
20. On average during the past seven days, how strong have been your feelings that others are talking about you? (ideas of reference, IOR); and
21. How strong have the voices or other hallucinations been on average during the past week, 0 to 10, with 10 being the strongest?; and Spaces 22–24 may be used for any other prominent psychotic symptoms. Alternatively, it may be used for a personalized "code word" the patient may use for his or her psychotic symptoms, for example, "signals", "weird feelings", or "fantasies".

4–5. Schizo-affective disorder and Schizophrenia with depression

These are diagnosed by DSM-IV criteria, which are hereby incorporated by reference. Psychotic symptoms (hallucinations, delusions, thought disorder, behavior disturbance, or negative symptoms) may be rated by the clinician and recorded in the spaces provided for Items 16 through 24 on severe depression diagnosis recording sheet 50.

6. Non-melancholic, non-psychotic severe unipolar maior depression (occasionally described as refractory or treatment-resistant depression):

The above are severe (and often treatment-refractory) unipolar depressions that do not fit in the categories B.1–B.5 above. Severity is indicated by high scores (generally several scores, for example 2 or more scores, of 7 or 8 or more) on diagnosis recording sheet 20 and the Despair Cluster of severe depression diagnosis recording sheet 50.

7. Bipolar depression:

This is a major depressive episode in a patient with a history of mania or hypomania (by DSM-IV criteria), which must be elicited explicitly. It is otherwise very often missed, and can be recognized by the following scoring features on diagnosis recording sheet 20.

a. Sleep disturbance is a key feature and can be tracked very well using Items 4a–4d.
   b. Energy disturbance is tracked with Item 8.
   c. Additional depression symptoms are tracked on the remainder of the diagnosis recording sheet 20, with additional severe depression symptoms tracked on the severe depression diagnosis recording sheet 50.
   d. Additional symptoms of mania or hypomania are tracked by writing these in as optional Items 22–24 on the severe depression diagnosis recording sheet 50.

Thus, based on the results obtained from the use of diagnosis sheet 20 and/or diagnosis sheet 50, those skilled in the art will be better able to administer suitable effective therapies to treat a patient's depressive symptoms. Such therapies are known to those skilled in the art and include, but are not limited to, medication therapies, bio-feedback therapies, light therapies, and counseling.

It should be noted, that the present invention permits a clinician, patient (individual) or other person administering the method to obtain immediate feedback and/or immediate outcome data with regard to the existence of any depressive symptoms in the individual who has provided answers to the questions posed (be they self-posed or otherwise).

Those skilled in the art will recognize that the embodiment(s) described above and illustrated in the attached drawings are intended for purposes of illustration only and that the subject invention may be implemented in various ways. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A method for determining the existence or non-existence of depression in an individual, the method including the steps of:

(A) asking the individual at least one question regarding at least one depressive criterion;
   (B) recording the individual's answer(s) to the at least one question; and
   (C) scoring the individual's answer(s) so as to determine the existence or non-existence of depression in the individual, wherein the questions are worded so as to elicit a verbal and/or non-verbal numerical response from 0 to 10, where 0 represents the non-existence of at least one depressive criterion and 10 represents the most severe manifestation of at least one depressive criterion, and wherein step (A) further comprises asking the individual additional questions regarding their sleeping habits and/or problems and the amount, if any, of any psychotropic medication(s) being taken, wherein the additional questions are worded so as to elicit a numerical response based upon the occurrence and/or frequency of selected sleeping habits and/or problems, and the amount of psychotropic medication(s), if any, being taken.

2. The method of claim 1, wherein the method is self-administered by the individual.

3. The method of claim 1, wherein the method is administered by a person other than a treating clinician.

4. The method of claim 1, wherein if the individual provides a two number numerical range answer to one or more of the questions the higher numerical value of each two number range is recorded as the score to the one or more questions.

5. The method of claim 1, wherein it the individual provides a two number numerical range answer to one or more questions the lower numerical value of each two number numerical range is recorded as the score to the one or more questions.

6. The method of claim 1, wherein if the individual provides a three number numerical range answer to one or more questions the middle numerical value of each three number numerical range is recorded as the score to the one or more questions.

7. The method of claim 1, wherein step (B) involves recording the individual's answers on a form specifically designed to correspond with the at least one question being asked.

8. The method of claim 1, wherein the method further comprises the additional steps of:

(D) asking the individual further questions regarding certain depression clusters, patterns and/or subtypes; and
   (E) scoring the individual's answer(s) so as to determine the subtype and severity of depression in the individual.

9. The method of claim 1, wherein the scoring of the individual's responses is used to determine a course of treatment for a depressive state.

10. The method of claim 8, wherein the method further comprises the additional step of:
(F) devising a course of treatment based on the information gathered in steps (A)–(E).

11. The method of claim 10, wherein steps (A)–(F) are repeated until complete or nearly-complete symptom clearing is achieved.

12. A method for determining the existence or non-existence of depression in an individual, the method including the steps of:
(A) asking the individual at least one question regarding at least one depressive criterion;
(B) recording the individual's answer(s) to the at least one question;
(C) scoring the individual's answer(s) so as to determine the existence or non-existence of depression in the individual;
(D) asking the individual further questions regarding certain depression clusters, patterns and/or subtypes; and
(E) scoring the individual's answer(s) so as to determine the subtype and severity of depression in the individual, wherein the questions are worded so as to elicit a verbal and/or non-verbal numerical response from 0 to 10, where 0 represents the non-existence of at least one depressive criterion and 10 represents the most severe manifestation of at least one depressive criterion, and
wherein the method further comprises repeating steps (A) through (E) at regular intervals so as to track an individual's progression or regression.

13. A method for determining the existence or non-existence of depression in an individual, the method including the steps of:
(A) asking the individual questions regarding depressive criteria;
(B) recording the individual's answers to the question; and
(C) scoring the individual's answers so as to determine the existence or non-existence of depression in the individual,
wherein the questions of step (A) include:
(1) On average for the past seven days up to right now, how severe would you say your discouragement and/or depression been with 10 being the worst possible and 0 being none at all?;
(2) On average for the past seven days up to right now, how severe would say your nervousness and/or anxiety has been, with 10 being the worst possible and 0 being none at all?;
(3) How much appetite disturbance have you had on average over the past seven days, with 10 being the worst and 0 being no disturbance?;
(4) How much sleep disturbance would you say you have had on average over the past seven days, with 10 being the worst and 0 being no sleep disturbance at all?;
(5) On average during the past seven days how much interference have you had with your interests, with 10 being the worst and 0 being no interference?;
(6) On average during the past seven days, how much interference have you had with your ability to experience pleasure, with 10 indicating complete interference with your ability to experience any pleasure, and 0 indicating no interference at all?;
(7) On average during the past seven days, how much interference have you had with your sex drive?;
(8) During the past seven days how much disturbance have you had, on average, with your energy, with 10 being total interference and 0 being no disturbance at all?;
(9) On average during the past seven days, how much interference have you experienced with thinking and/or concentrating, with 10 indicating total incapacitation, and 0 indicating no interference at all?;
(10) During the past seven days on average how strong have your feelings of worthlessness, self-blame, and guilt been, on a scale of 0 to 10, with 0 being no strong feelings of worthlessness, self-blame, and guilt and 10 nearly continuous strong feelings of worthlessness, self-blame, and guilt?;
(11) On average during the past seven days, how strong have your thoughts of death been, with 10 indicating that death has been your only topic of thought and 0 indicating that you haven't thought about death at all?;
(12) On average during the past seven days how strong have your thoughts of suicide been, with 10 being the maximum and 0 being none at all?;
(13) Are you currently (right at this moment) planning or intending suicide or homicide?;
(14) Would you say that during the past seven days you have been, on average, more nervous, more tired, "50-50", or neither nervous or tired?;
(15) Which psychotropic medications (or medications for depression, anxiety, fears, etc.) are you currently taking and what doses?;
(16) Which other medications are you taking and at what doses?
(17) Which possible medication side effects are you experiencing, and also rate the severity of any such side effects with 0 indicating no severity and 10 indicating extreme severity 10?; and
(18) What has been going on in your life that may have an effect on your depression?.

14. The method of claim 13, wherein the method is self-administered by the individual.

15. The method of claim 13, wherein the method is administered by a person other than a treating clinician.

16. The method of claim 13, wherein if the individual provides a two number numerical range answer to one or more questions the higher numerical value of each two number range is recorded as the score to the one or more questions.

17. The method of claim 13, wherein if the individual provides a two number numerical range answer to one or more questions the lower numerical value of each two number numerical range is recorded as the score to the one or more questions.

18. The method of claim 13, wherein if the individual provides a three number numerical range answer to one or more questions the middle numerical value of each three number numerical range is recorded as the score to the one or more questions.

19. The method of claim 13, wherein step (B) involves recording the individual's answers on a form specifically designed to correspond with the questions being asked.

20. The method of claim 13, wherein the method further comprises asking the following questions immediately after question (4a) in step (A):
(4b) How many hours sleep per night have you been getting during the past week or What range of hours of sleep per night?;

(4c) How many (if any) of the past seven nights have you been awakened in the middle of the night and couldn't fall back asleep for an hour or more?;

(4d) How many (if any) of the past seven mornings have you been awakened in the early morning (e.g. between 3 a.m. and 7 a.m.) and couldn't fall back to sleep for an hour or more?.

21. The method of claim 13, wherein the method further comprises the additional steps of:

(D) asking the individual further questions regarding certain depression clusters, patterns and/or subtypes; and (E) scoring the individual's answer so as to determine the subtype and severity of depression in the individual.

22. The method of claim 21, wherein the scoring of the individual's responses is used to determine a course of treatment for a depressive state.

23. A method for determining the existence or non-existence of depression in an individual, the method including the steps of:

(A) asking the individual at least one question regarding at least one depressive criterion which requires a response, wherein the at least one question is designed to elicit a verbal and/or non-verbal numerical response from 0 to 10;

(B) recording the individual's numerical response(s) to the at least one question;

(C) scoring the individual's answer(s) so as to determine the existence or non-existence of depression in the individual; and (D) repeating steps (A) through (C) at regular intervals so as to track an individual's progression or regression.

24. The method of claim 23, wherein the method further comprises the additional step of:

(E) devising a course of treatment based on the information gathered in steps (A)–(D).

25. The method of claim 24, wherein steps (A)–(E) are repeated until complete or nearly-complete symptom clearing is achieved.

* * * * *